(12) United States Patent
Saba et al.

(10) Patent No.: US 10,572,024 B1
(45) Date of Patent: Feb. 25, 2020

(54) HAND TRACKING USING AN ULTRASOUND SENSOR ON A HEAD-MOUNTED DISPLAY

(71) Applicant: Facebook Technologies, LLC, Menlo Park, CA (US)

(72) Inventors: Elliot Saba, Redmond, WA (US); Robert Y. Wang, Kirkland, WA (US); Christopher David Twigg, San Francisco, CA (US); Ravish Mehra, Redmond, WA (US)

(73) Assignee: Facebook Technologies, LLC, Menlo Park, CA (US)

( * ) Notice: Subject to any disclaimer, the term of this patent is extended or adjusted under 35 U.S.C. 154(b) by 97 days.

(21) Appl. No.: 15/668,418

(22) Filed: Aug. 3, 2017

Related U.S. Application Data

(60) Provisional application No. 62/401,090, filed on Sep. 28, 2016.

(51) Int. Cl.
| | |
|---|---|
| *G06F 3/01* | (2006.01) |
| *G02B 27/01* | (2006.01) |
| *G01N 29/12* | (2006.01) |
| *G06N 20/00* | (2019.01) |

(52) U.S. Cl.
CPC ............ *G06F 3/017* (2013.01); *G01N 29/12* (2013.01); *G02B 27/0149* (2013.01); *G06N 20/00* (2019.01); *G02B 2027/0138* (2013.01)

(58) Field of Classification Search
CPC ... G06T 19/006; G06T 19/003; A63F 13/428; A63F 13/26; A63F 13/23; A63F 13/24; A63F 13/213; A63F 13/426; A63F 13/5255; A63F 13/98; A63F 13/215; A63F 2300/538; A63F 13/25; G06F 2203/04101; G06F 3/005; G06F 3/017; G06F 3/01; G09G 5/00; H04N 13/271
USPC .......................................................... 345/156
See application file for complete search history.

(56) References Cited

U.S. PATENT DOCUMENTS

| | | | | |
|---|---|---|---|---|
| 9,778,749 | B2 * | 10/2017 | Poupyrev | G06F 3/017 |
| 9,921,657 | B2 * | 3/2018 | Sprenger | G06F 3/017 |
| 10,037,474 | B2 * | 7/2018 | Holz | G06K 9/00355 |

(Continued)

FOREIGN PATENT DOCUMENTS

| | | | |
|---|---|---|---|
| CN | 106203380 A | * | 12/2016 |
| JP | 2010218365 A | * | 9/2010 |

*Primary Examiner* — Bryan Earles
(74) *Attorney, Agent, or Firm* — Fenwick & West LLP

(57) ABSTRACT

A head-mounted display (HMD) tracks a user's hand positions, orientations, and gestures using an ultrasound sensor coupled to the HMD. The ultrasound sensor emits ultrasound signals that reflect off the hands of the user, even if a hand of the user is obstructed by the other hand. The ultrasound sensor identifies features used to train a machine learning model based on detecting reflected ultrasound signals. For example, one of the features is the time delay between consecutive reflected ultrasound signals detected by the ultrasound sensor. The machine learning model learns to determine poses and gestures of the user's hands. The HMD optionally includes a camera that generates image data of the user's hands. The image data can also be used to train the machine learning model. The HMD may perform a calibration process to avoid detecting other objects and surfaces such as a wall next to the user.

18 Claims, 9 Drawing Sheets

Obstructed Hand in Scissor Position

(56) References Cited

U.S. PATENT DOCUMENTS

| | | | | |
|---|---|---|---|---|
| 2012/0001875 A1* | 1/2012 | Li | G01S 7/5273 | 345/177 |
| 2012/0243374 A1* | 9/2012 | Dahl | G06F 3/043 | 367/93 |
| 2012/0280900 A1* | 11/2012 | Wang | G06F 3/0488 | 345/156 |
| 2012/0309532 A1* | 12/2012 | Ambrus | G06F 3/0425 | 463/36 |
| 2013/0229508 A1* | 9/2013 | Li | G06F 1/3287 | 348/77 |
| 2014/0045594 A1* | 2/2014 | Marks | G06F 3/017 | 463/36 |
| 2014/0243614 A1* | 8/2014 | Rothberg | A61B 8/13 | 600/301 |
| 2015/0029092 A1* | 1/2015 | Holz | G06F 3/017 | 345/156 |
| 2016/0274732 A1* | 9/2016 | Bang | G06F 3/017 | |
| 2017/0060254 A1* | 3/2017 | Molchanov | G06F 3/011 | |
| 2017/0262045 A1* | 9/2017 | Rouvinez | G06T 19/006 | |
| 2017/0329004 A1* | 11/2017 | Yoo | G01S 7/52003 | |
| 2018/0188353 A1* | 7/2018 | Chen | G01S 5/16 | |

* cited by examiner

Obstructed Hand in Fist Position

Obstructed Hand in Scissor Position

700

Capture images in a region in front of a HMD worn by a user to generate image data.
710

Emit an ultrasound signal towards the region.
720

Detect a reflected version of the emitted ultrasound signal.
730

Generate ultrasound data.
740

Process the image data and the ultrasound data to determine a pose or a gesture of the user's hands.
750

FIG. 7

HAND TRACKING USING AN ULTRASOUND SENSOR ON A HEAD-MOUNTED DISPLAY

CROSS-REFERENCE TO RELATED APPLICATION

This application claims the benefit of and priority to U.S. Provisional Application No. 62/401,090 filed Sep. 28, 2016, which is incorporated by reference herein in its entirety.

BACKGROUND

The present disclosure relates to a hand tracking system and method, for example, a hand tracking system and method for determining hand poses and gestures of an obstructed hand using an ultrasound sensor on a head-mounted display.

It is known that motion tracking systems can use image processing to determine the position and gestures of a person. Existing systems can use different types of cameras (for example, structured light scanners, RGB cameras, and depth cameras) to capture images and video of a person. However, the person must be in the field of view of the camera. For instance, if the person's right hand is obstructed by the person's left hand, then the camera cannot capture images or video of the right hand. Accordingly, image based motion tracking systems are unable to determine the position of obstructed body parts.

An ultrasound sensor can determine the distance between the ultrasound sensor and another object or surface. The ultrasound sensor emits an ultrasound signal, i.e., a sound wave between 20 kiloHertz and 200 megaHertz. The ultrasound signal reflects off of the object or surface, and the ultrasound sensor detects the reflected ultrasound signal. The ultrasound sensor determines the distance based on the known speed of sound (approximately 340 meters per second) and the time of flight of the reflected ultrasound signal.

SUMMARY

Embodiments relate to a system for determining hand poses and gestures of a user wearing a head-mounted display (HMD). The HMD includes an ultrasound sensor that has at least one ultrasound transmitter configured to emit an ultrasound signal and at least one ultrasound receiver configured to detect a reflected ultrasound signal. For example, the emit ultrasound signal reflects off of a hand of the user and is detected by the ultrasound receiver.

The HMD includes a processor configured to receive image data from a camera and receive ultrasound data from the ultrasound sensor. The processor determines hand poses and gestures of a hand of the user based on the image data and the ultrasound data. A hand pose indicates a position and/or orientation of the user's hands in at least two dimensions. Hand gestures include, for example, waving a hand, pointing at least one finger of a hand, grabbing an object using a hand, and holding a hand in a stable position. The processor can also determine that one of the user's hands is obstructed based on the image data.

In some embodiments, the ultrasound sensor generates the emitted ultrasound signal based on a windowed cardinal sine function. Further, the processor may modify the ultrasound data using pulse compression. In some embodiments, the processor retrieves calibration data and determines the hand poses and gestures also based on the calibration data.

In some embodiments, the processor uses a machine learning model trained with feature vectors based on previous ultrasound data. The processor provides the image data and the ultrasound data as input to the machine learning model. The processor uses the machine learning model to determine hand poses and gestures of the user's hands. The feature vectors may include a time delay between a set of consecutive reflected ultrasound signals detected by the ultrasound sensor.

BRIEF DESCRIPTION OF DRAWINGS

FIG. 7 is a flowchart illustrating a process of performing hand tracking using the head-mounted display, according to one embodiment.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Reference will now be made in detail to embodiments, examples of which are illustrated in the accompanying drawings. In the following detailed description, numerous specific details are set forth in order to provide a thorough understanding of the various described embodiments. However, the described embodiments may be practiced without these specific details. In other instances, well-known methods, procedures, components, circuits, and networks have not been described in detail so as not to unnecessarily obscure aspects of the embodiments.

Exemplary System Overview

Figure 1:
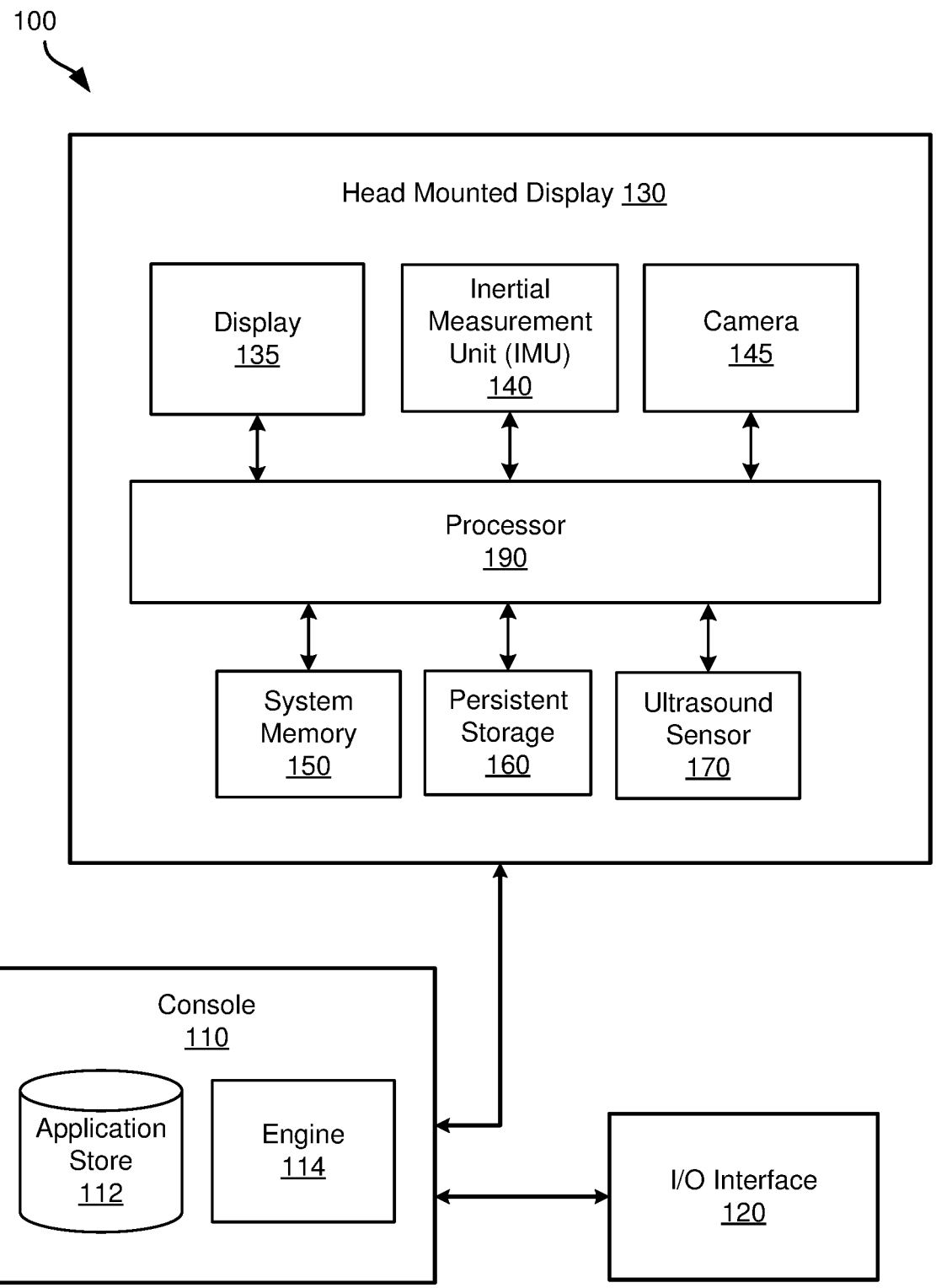
FIG. 1 is a diagram of a system for hand tracking using a head-mounted display, according to one embodiment.

FIG. 1 is a diagram of a system 100 for hand tracking using a head-mounted display, according to one embodiment. In some embodiments, the system 100 operates in a virtual reality (VR), augmented reality (AR), or mixed reality (MR) environment. The system 100 shown in FIG. 1 comprises a head-mounted display (HMD) 130 and an input/output (I/O) interface 120 that are each coupled to a console 110. While FIG. 1 shows an example system 100 including one HMD 130 and one I/O interface 120, in other embodiments, any number of these components are included in the system 100. For example, there are multiple HMDs 130 each having an associated I/O interface 120 and each communicating with the console 110. In alternative configurations, different and/or additional components may be included in the system 100.

The HMD 130 presents content to a user. Examples of content presented by the HMD 130 include one or more images, video, audio, or some combination thereof. In some embodiments, audio is presented via an external device (e.g., speakers and/or headphones) that receives audio information from the HMD 130, the console 110, or both, and presents audio data based on the audio information.

The HMD 130 includes a display 135, inertial measurement unit (IMU) 140, camera 145, system memory 150, persistent storage 160, and ultrasound sensor 170, each communicatively coupled to the processor 190. The processor 190 is embodied as one or more integrated circuit (IC) chips and performs various data processing processes, which is further described below in detail with reference to FIG. 2. HMD 130 is only one example of an HMD, and in other embodiments, the HMD 130 may have more or fewer components, some of which may be combined into a single component or have a different configuration or arrangement. The components of the HMD 130 are embodied in hardware, software, firmware or a combination thereof.

The display 135 displays images and/or video to the user as generated by the HMD 130, console 110, or another device. The display 135 may comprise a single electronic display or multiple electronic displays (e.g., a display for each eye of a user). Examples of the display 135 include: a liquid crystal display (LCD), an organic light emitting diode (OLED) display, an active-matrix organic light-emitting diode display (AMOLED), or some combination thereof.

The IMU 140 is an electronic device that generates position data based on measurement signals received from one or more position sensors. A position sensor generates one or more measurement signals in response to motion of the HMD 130. Examples of position sensors include accelerometers, gyroscopes, and magnetometers. The position sensors may be located external to and/or internal to the IMU 140.

The camera 145 is an electronic device that captures image data and may be embodied, for example, as an image sensor, complementary metal-oxide-semiconductor (CMOS) active sensor, video camera, RGB camera, infrared camera, depth sensor, or other types of imaging devices. The camera 145 may include a filter to pass only certain wavelengths of light (e.g., visible light or infrared light). In some embodiments, the camera 145 generates raw image data that is sent to the processor 190 for further processing. The image data may be displayed on the display 135, stored in system memory 150, persistent storage 160, or sent to a remote computing device, e.g., the console 110, via a network connection.

The system memory 150 stores instructions for execution by the processor 190 and stores data processed by the processor 190. The system memory 150 may be embodied a dynamic random access memory (DRAM), synchronous DRAM (SDRAM), double data rate (DDR, DDR2, DDR3, etc.), any combination thereof, or any other type of memory.

The persistent storage 160 stores data in a non-volatile manner. The persistent storage 160 retains data even when the HMD 130 is not powered. The persistent storage 160 may be embodied as read-only memory (ROM), flash memory, or any other type of non-volatile random access memory devices.

The ultrasound sensor 170 includes one or more ultrasound transmitters and one or more ultrasound receivers. The ultrasound transmitter emits ultrasound signals and the ultrasound receiver detects audio signals, which may include ultrasound signals. The ultrasound transmitters and receivers may be a capacitive type, piezoelectric type, or any other type of transducer suitable to emit or detect ultrasound signals. In one embodiment, the center frequency of the ultrasound transmitter and/or ultrasound receiver is approximately 40 kiloHertz. The ultrasound sensor 170 may include a hardware filter to remove unwanted noise (e.g., audio outside of the ultrasound frequency range) from the received ultrasound signals, and thus improve the signal-to-noise ratio before subsequent processing. In some embodiments, the ultrasound sensor 170 is protected by a cover such that the ultrasound sensor 170 is water resistant or waterproof. Further, the ultrasound sensor 170 may include a reflector (e.g., having a conical shape or a curved surface) to increase the beam width of the emitted ultrasound signals.

The I/O interface 120 is a device that allows a user to send action requests to the console 110. An action request is a request to perform a particular action. For example, an action request may be to start or end an application or to perform a particular action within the application. The I/O interface 120 may include one or more input devices, e.g., a keyboard, mouse, or game controller. An action request received by the I/O interface 120 is communicated to the console 110, which performs an action corresponding to the action request. In some embodiments, the I/O interface 120 may provide haptic feedback to the user in accordance with instructions received from the console 110. For example, haptic feedback is provided when an action request is received.

The console 110 provides content to the HMD 130 for presentation to a user in accordance with information received from the HMD 130 and/or the I/O interface 120. In the example shown in FIG. 1, the console 110 includes an application store 112 and an engine 114. Other embodiments of the console 110 have different modules than those described in conjunction with FIG. 1. Similarly, the functions further described below may be distributed among components of the console 110 in a different manner than is described here.

The application store 112 stores one or more applications for execution by the console 110. An application is a group of instructions, that when executed by the processor 190, generates content for presentation to the user. Content generated by an application may be in response to inputs received from the user via movement of the HMD 130 or the I/O interface 120. Examples of applications include: gaming applications, conferencing applications, video playback application, or other suitable applications.

The engine 114 executes applications within the system 100, e.g., using a processor. The engine 114 may receive and process position information, acceleration information, velocity information, image data, or some combination thereof. In some embodiments, the engine 114 generates hand poses and gestures a user's hands based on information received from the HMD 130 or I/O interfaces 120. Based on the hand tracking information, the engine 114 generates hand positions and gestures of an avatar corresponding to a user wearing the HMD 130. For instance, a waving hand gesture corresponds to hand wave that the user performs in real life. In some embodiments, the system does not include a console 110, and the HMD 130 performs the functionality of the console 110.

Exemplary Processor

Figure 2:
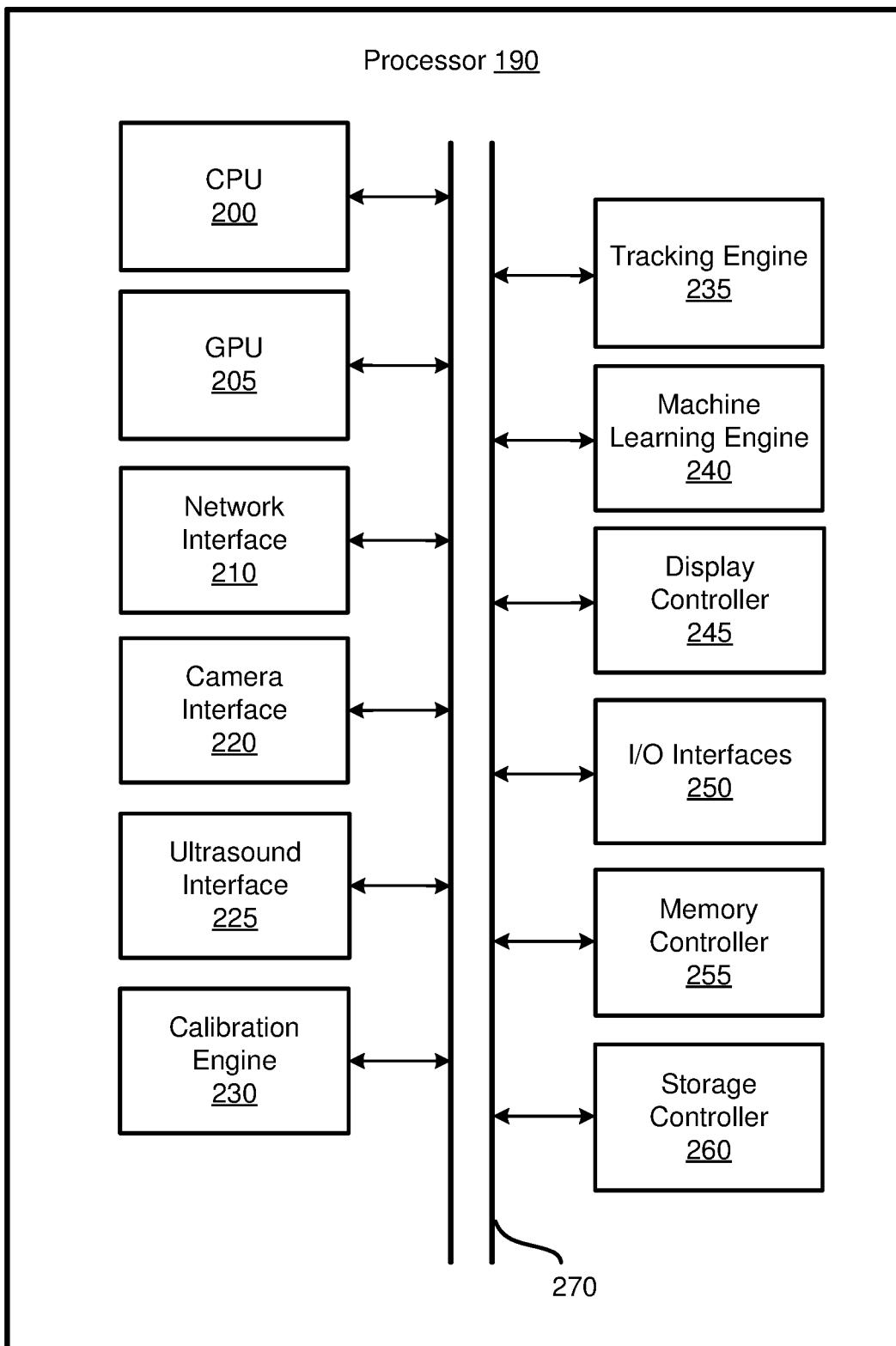
FIG. 2 is a block diagram illustrating components in a processor of the head-mounted display, according to one embodiment.

FIG. 2 is a block diagram illustrating components in the processor 190 of the head-mounted display 130, according to one embodiment. The processor 190 may include, among other subcomponents, a central processor unit (CPU) 200, graphics processor unit (GPU) 205, network interface 210, camera interface 220, ultrasound interface 225, calibration engine 230, tracking engine 235, machine learning engine 240, display controller 245, I/O interfaces 250, memory controller 255, and storage controller 260, each connected to the bus 270. The processor 190 may include more or fewer component than those shown in FIG. 2. In some embodiments, the console 110 performs one or more functions of the HMD 130.

The CPU 200 may be a general-purpose or embedded processor using any suitable instruction set architecture (ISA), e.g., x86, PowerPC, SPARC, RISC, ARM, or MIPS ISAs. The CPU 200 is configured to execute instructions defined in the ISA. In multiprocessor system embodiments, the processor 190 includes multiple CPUs, each of which may implement the same or different ISAs.

The GPU 205 is a graphics processing circuitry for processing graphical data. In one embodiment, the GPU 205 renders objects to be displayed on the display 135 of the HMD 130. The GPU 205 may include multiple graphics processors that each executes graphics software to perform graphics operations, e.g., hard acceleration of graphics operations.

The network interface 210 facilitates data exchange between the HMD 130 and other devices via one or more networks. For example, the HMD 130 receives video or image data from the console 110 and stores the received data in the system memory 150 for subsequent processing (e.g., by the camera interface 220). The networks may include Local Area Networks (LAN), e.g., an Ethernet or corporate network, Wide Area Networks (WANs), BLUETOOTH®, WIFI, or any other suitable type of network.

The camera interface 220 is circuitry for interfacing with the camera 145. The camera interface 220 receives image data from the camera 145 and processes the image data to determine hand poses and gestures of a user, e.g., the position and orientation of the user's hands in at least two dimensions. In some embodiments, the camera interface 220 implements one or more different types of image processing techniques such as color based filtering (e.g., based on the color of a user's hands), RGB or HSV color modeling, histogram based object tracking, Bayesian networks, Kalman filtering, fingertip tracking, or hand contour tracking, to process the image data.

The ultrasound interface 225 is circuitry for interfacing with the ultrasound sensor 170. The ultrasound interface 225 sends a transmitted signal to the ultrasound sensor 170. Based on the transmitted signal, the ultrasound sensor 170 emits an ultrasound signal using an ultrasound transmitter. The ultrasound interface 225 receives an ultrasound signal from an ultrasound receiver of the ultrasound sensor 170 and generates ultrasound data based on the received ultrasound signal. The received ultrasound signal may include ultrasound signals transmitted by the ultrasound transmitter that reflect off of an object or surface.

In some embodiments, the ultrasound interface 225 performs pulse compression. The ultrasound interface 225 modulates the transmitted signal, for example, using a particular carrier frequency and sweeping across a certain frequency band. The transmitted signal can be a windowed sinc (i.e., cardinal sine) function, another sinusoidal function, or any other type of function (e.g., a rectangle or saw-tooth function). Alternatively, the ultrasound interface 225 can perform pulse compression using phase modulation, for example, using Barker codes.

Since the received ultrasound signal from an ultrasound receiver may have white Gaussian noise, the ultrasound interface 225 may perform matched filtering to detect the ultrasound signal from the noise. The ultrasound interface 225 correlates the transmitted signal with the received ultrasound signal. For example, the ultrasound interface 225 convolves the received ultrasound signal with a conjugated version of the transmitted signal. By performing pulse compression, the ultrasound interface 225 may improve the signal-to-noise ratio of processed ultrasound data and increase the range resolution of the ultrasound sensor 170.

In some embodiments, the ultrasound interface 225 can process ultrasound data and motion data to account for the Doppler Effect. In an example use case, the user wearing the HMD 130 also wears a glove type I/O interface 120 (on one or both hands) that includes an IMU substantially the same as the IMU 140 of the HMD 130. The ultrasound interface 225 receives motion data from the IMU 140 and from the IMU of the gloves and determines a discrepancy in the frequency of the ultrasound data based on the motion data. In other words, the ultrasound interface 225 can determine motion of the hands relative to the HMD 130 also in motion. In other embodiments, the ultrasound interface 225 can use other types of algorithms to account for Doppler shift without necessarily using motion data.

The calibration engine 230 performs a calibration process to generate calibration data. In one embodiment, during the calibration process, the calibration engine 230 provides instructions to a user wearing the HMD 130. The HMD may provide an instruction as an image or video on the display 135 and/or via audio using a speaker of the HMD. The instructions inform the user to look in one or more directions, or look toward one or more objects (e.g., a table, chair, television, another person, etc.) in the vicinity of the user.

For example, the user is located inside a room and an instruction informs the user to look toward a wall of the room. In coordination with the instruction, the ultrasound interface 225 sends a transmitted signal for the ultrasound sensor 170 to emit an ultrasound signal. The ultrasound signal reflects off of the wall, and the ultrasound sensor 170 receives the reflected ultrasound signal. The ultrasound interface 225 generates ultrasound data based on the reflected ultrasound signal. The calibration engine 230 generates calibration data based on the ultrasound data and the instruction. The calibration data may include a mapping of an attribute of the instruction to an attribute of the ultrasound data.

For example, the calibration data maps an identifier describing the wall to an average amplitude value of the ultrasound data, or to a time of flight value of the reflected ultrasound signal. Thus, at a later time, if the processor 190 processes calibration data with similar (or the same) average amplitude value or time of flight value, the processor 190 (e.g., via a machine learning model, which is further described below) can determine that the user is likely looking at the same wall. In other words, the processor 190 can be calibrated to recognize particular surfaces or objects in the vicinity of the user.

The tracking engine 235 uses image data processed by the camera interface 220 and/or ultrasound data processed by the ultrasound interface 225 to determine poses and gestures of a user wearing the HMD 130. A pose can describe the position and/or orientation of one or more body parts of the user. For example, hand poses and gestures indicate that a hand of a user is in a particular position (e.g., in 2D or 3D space), that the hand is in a particular orientation (e.g., palms facing up, down, left, or right), or that the hand is performing a particular gesture (e.g., waving, pointing one or more fingers, making a fist, grabbing an object, holding in steady place, etc.). Hand gestures can indicate a speed at which the user is performing the gestures, e.g., whether the user is slowly or vigorously waving one of the user's hands, or a number of times the user performed a given gesture.

In one example use case, both hands of a user are in the field of view of the camera 145. Accordingly, the tracking engine 235 can use the image data to determine the hand poses and gestures of the user because neither hand is obstructed from the view of the camera 145. However, in a different example use case, one or both hands of the user are not in the field of view of the camera. For instance, one hand is obstructing the other hand. In this case, the image data may not have sufficient information about the obstructed hand. Thus, the tracking engine 235 also uses the ultrasound data to determine the hand poses and gestures of the user.

In some embodiments, the tracking engine 235 determines the hand poses and gestures using a lookup table of rules. In particular, the lookup table includes rules that map attributes of image data and ultrasound data to particular positions, orientations, and gestures of different body parts of a user. For example, a rule maps a time of flight value of a reflected ultrasound signal to a certain position of the user's hand. Another rule maps an audio signature (e.g., represented by a sinusoidal function) of a reflected ultrasound signal to a certain gesture of the user's hand. In some embodiments, the tracking engine 235 determines the hand poses and gestures using one or more machine learning models.

The machine learning engine 240 uses machine learning techniques to train one or more machine learning models. Machine learning techniques include, for example, linear regression, decision trees, support vector machines, classifiers (e.g., a Naive Bayes classifier), and gradient boosting. The machine learning engine 240 can train machine learning models using feature vectors identified based on information from ultrasound data previously processed by the ultrasound interface 225 and/or image date previously processed by the camera interface 220. The machine learning models can determine hand poses and gestures of a user wearing the HMD 130 based on input image data and/or the ultrasound data. The machine learning models and feature vectors are further described below in detail with reference to FIG. 7.

The display controller 245 is circuitry for sending image or video data to be displayed on the display 135. The display controller 245 receives data from the CPU 200, GPU 205, camera interface 220, and/or system memory 150, and processes the data into a suitable format for display on the display 135 of the HMD 130.

The memory controller 255 is circuitry for communicating with the system memory 150. The memory controller 255 may read data from system memory 150 for processing by other components of the processor 190. Further, the memory controller 255 may write data to system memory 150 received from various components of the processor 190.

The storage controller 260 is circuitry for communicating with the persistent memory 160. The storage controller 260 may read data from persistent memory 160 for processing by other components of the processor 190. Further, the storage controller 260 may write data to persistent memory 160 received from various components of the processor 190.

In some embodiments, one or more components of the processor 190, or some functionality of these components, may be performed by software components executed on the CPU 200 or GPU 205. Such software components may be stored in system memory 150, persistent storage 160, or any other device communicating with the HMD 130 via the network interface 210.

Exemplary Head-Mounted Display

Figure 3:
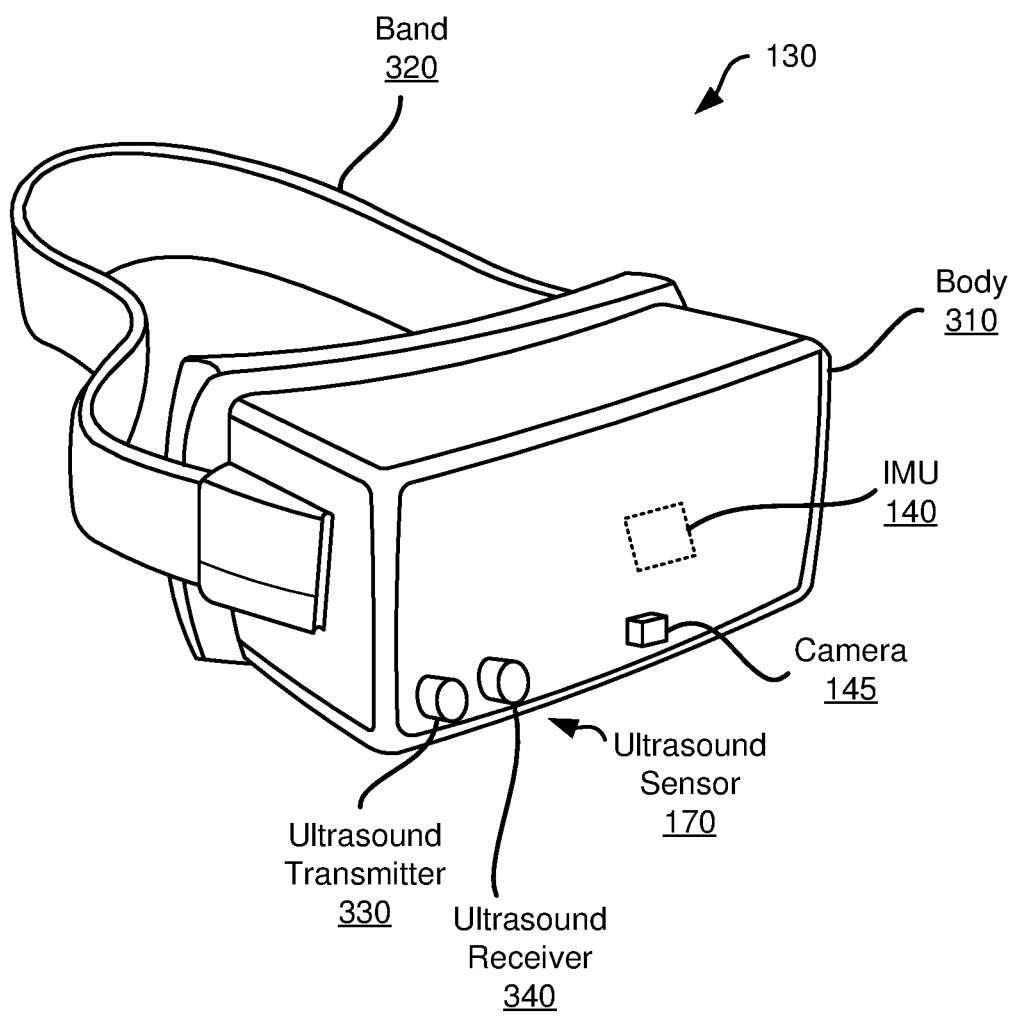
FIG. 3 is a perspective diagram of the head-mounted display, according to one embodiment.

FIG. 3 is a perspective diagram of the HMD 130, according to one embodiment. The HMD 130 includes a body 310 coupled to a band 320. The ultrasound sensor 170, camera 145, and IMU 140 are coupled to the body 310. The ultrasound sensor 170 includes an ultrasound transmitter 330 and an ultrasound receiver 340. In the embodiment shown by FIG. 3, the ultrasound transmitter 330, ultrasound receiver 340, and camera 145 are each coupled toward the bottom edge of the front face of the body, though in other embodiments, these components may be coupled to any other face of the body (e.g., the top, bottom, left, or right face), and may not necessarily be coupled to the same face. Furthermore, the ultrasound transmitter 330, ultrasound receiver 340, and camera 145 may each be facing in the same direction. A user wearing the HMD 130 can use the band 320 to hold the HMD 130 in place on the head of the user.

Example Hand Tracking Configurations

Figure 4A:
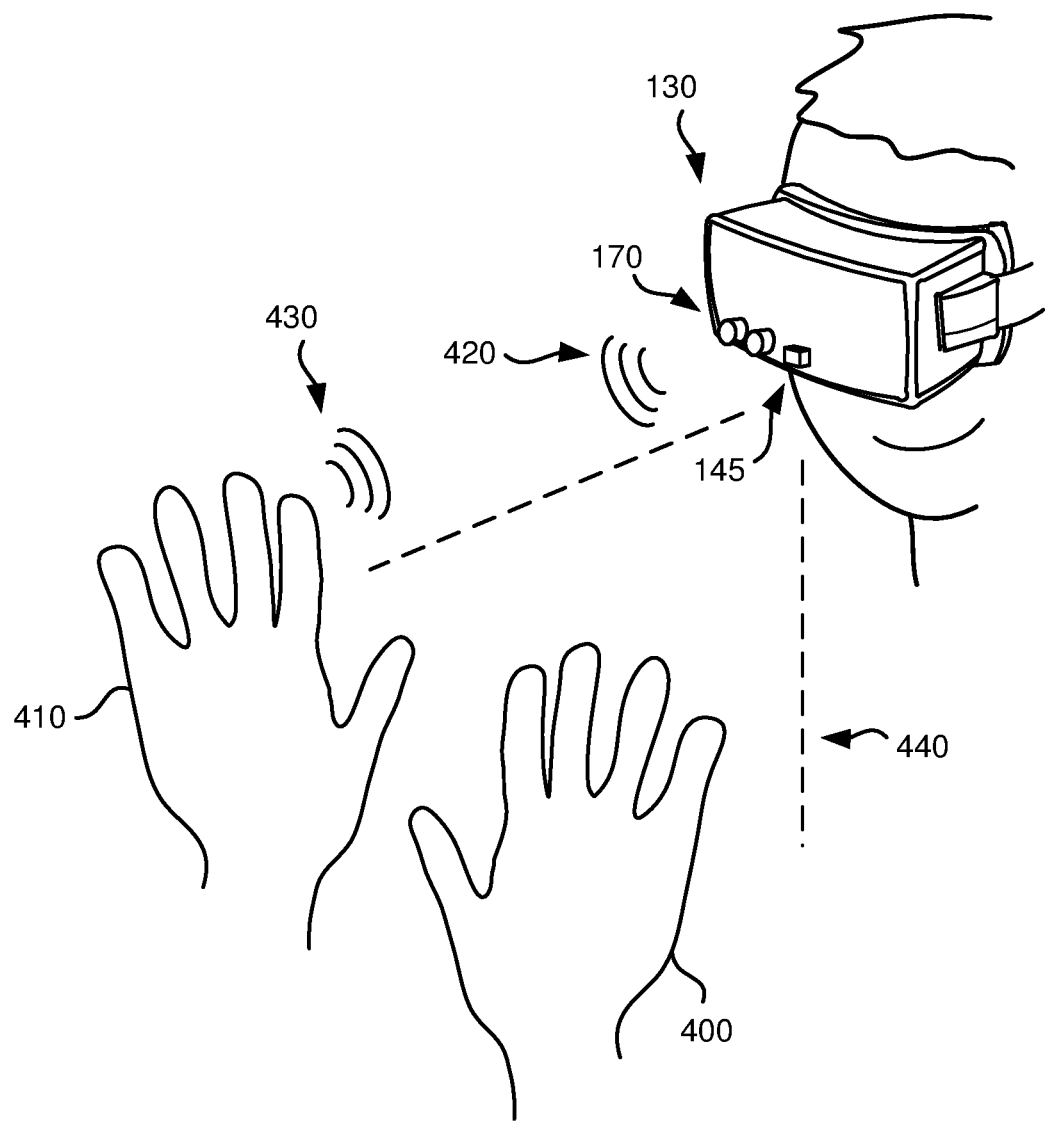
FIG. 4A is a diagram illustrating hand tracking using a head-mounted display with a camera, according to one embodiment.

FIG. 4A is a diagram illustrating hand tracking using a HMD 130 with a camera 145, according to one embodiment. The left hand 400 and right hand 410 of a user wearing the HMD 130 are positioned in front of the HMD 130. In particular, an ultrasound signal 420 emitted by the ultrasound sensor of the HMD 130 is reflected off of one or both hands of the user. Further, the ultrasound receiver of the HMD 130 receives the reflected ultrasound signal 430. The hands of the user are in the field of view 440 of the camera 145. Thus, the camera 145 can capture image data of the user's hands.

Figure 4B:
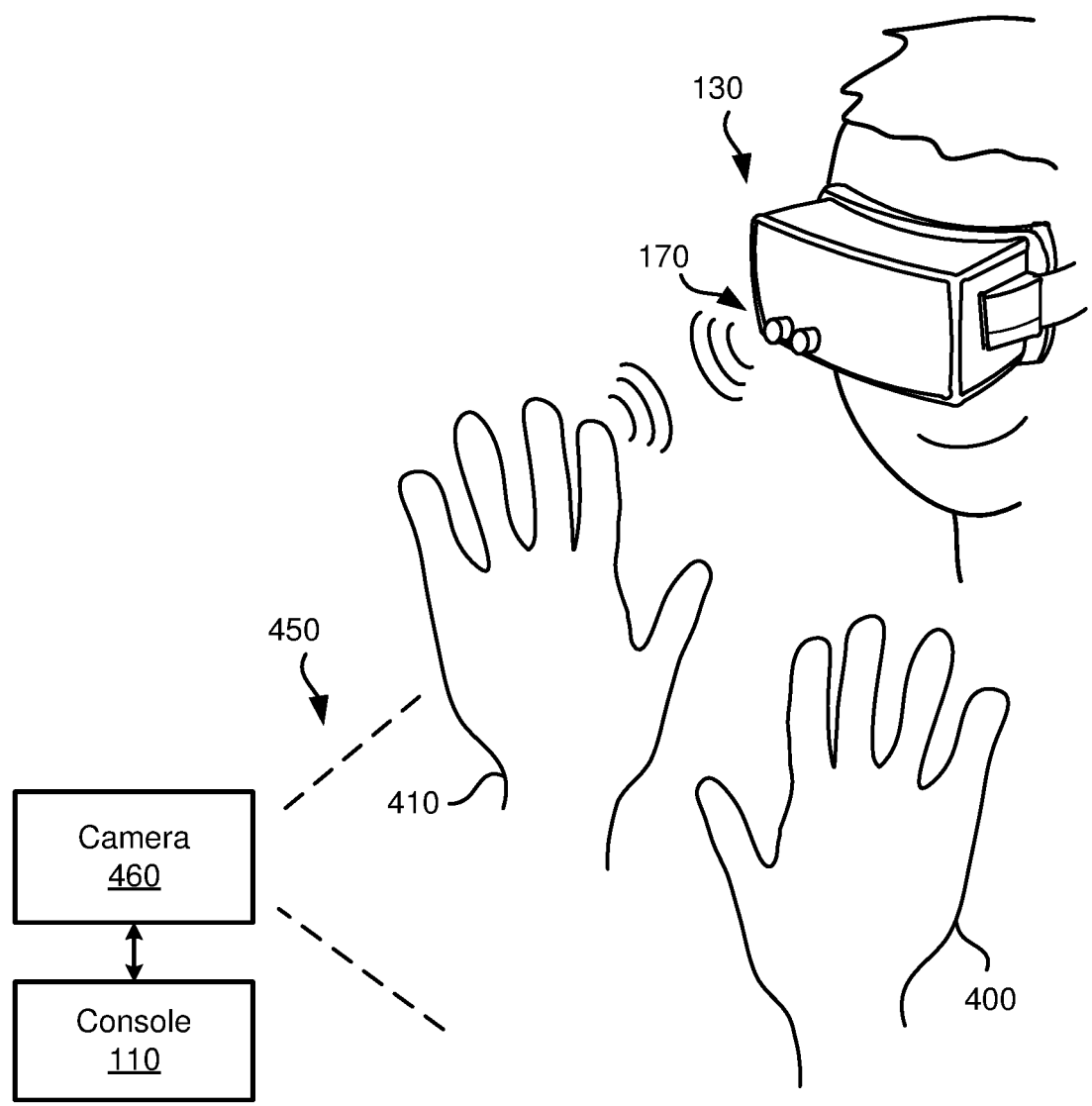
FIG. 4B is a diagram illustrating hand tracking using a head-mounted display with a camera separate from the head-mounted display, according to one embodiment.

FIG. 4B is a diagram illustrating hand tracking using a HMD 130 with a camera 460 separate from the HMD 130, according to one embodiment. In contrast with the HMD 130 shown in FIG. 4A, the HMD 130 shown in FIG. 4B does not include a camera. Instead, a camera 460 is coupled to the console 110. Since both hands of the user are in the field of view 450 of the camera 460, the camera 460 can also capture image data of the user's hands.

In some embodiments, the HMD 130 does not include an ultrasound sensor 170. Instead, an ultrasound sensor 170 separate from the HMD 130 is coupled to the console 110. The ultrasound sensor 170 faces the user's hands such that ultrasound signals emitted by the ultrasound sensor 170 are reflected back toward the ultrasound sensor 170.

Figure 5A:
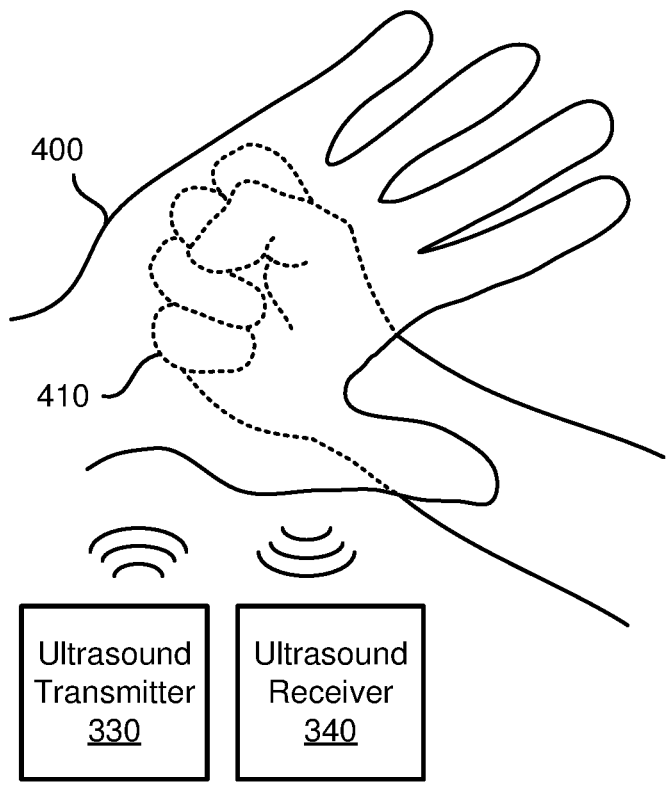
FIG. 5A is a diagram illustrating an obstructed hand of a user in a first position, according to one embodiment.

FIG. 5A is a diagram illustrating an obstructed hand of a user in a first position, according to one embodiment. FIG. 5A is shown from the perspective of the HMD 130 worn by the user in FIG. 4A. The right hand 410 is in a "fist" position and is obstructed by the left hand 400. Since the right hand 410 is obstructed, a camera coupled to the HMD 130 may not be able to capture image data of the right hand 410, but rather, only of the un-obstructed left hand 400. Similarly, in an embodiment where the camera is separate from the HMD 130 (e.g., as shown in FIG. 4B), the camera may only be able to capture image data of one hand of the user, and not the other obstructed hand.

Figure 5B:
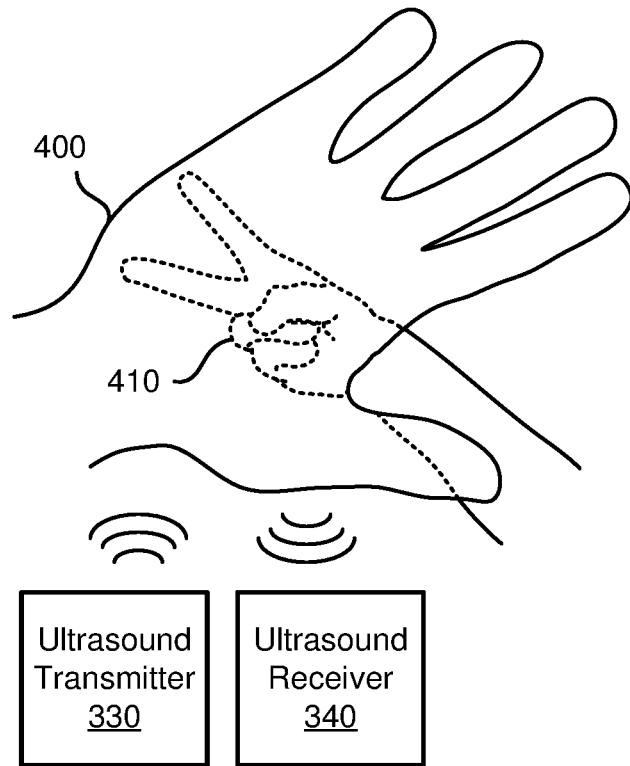
FIG. 5B is a diagram illustrating the obstructed hand of the user in a scissor position, according to one embodiment.

FIG. 5B is a diagram illustrating the obstructed hand of the user in a scissor position, according to one embodiment.

Similar to FIG. 5A, the diagram is shown from the perspective of the HMD 130 worn by the user in FIG. 4A. The right hand 410 is in a "scissor" position (e.g., the index finger and middle finger are pointed outward) and is obstructed by the left hand 400. Since the right hand 410 is obstructed in the embodiments shown in FIGS. 5A-B, the HMD 130 may not be able to distinguish the "fist" and "scissor" positions of the right hand 410 based only on the corresponding image data processed by the camera interface 220.

Example Ultrasound Data Processing

Figure 6A:
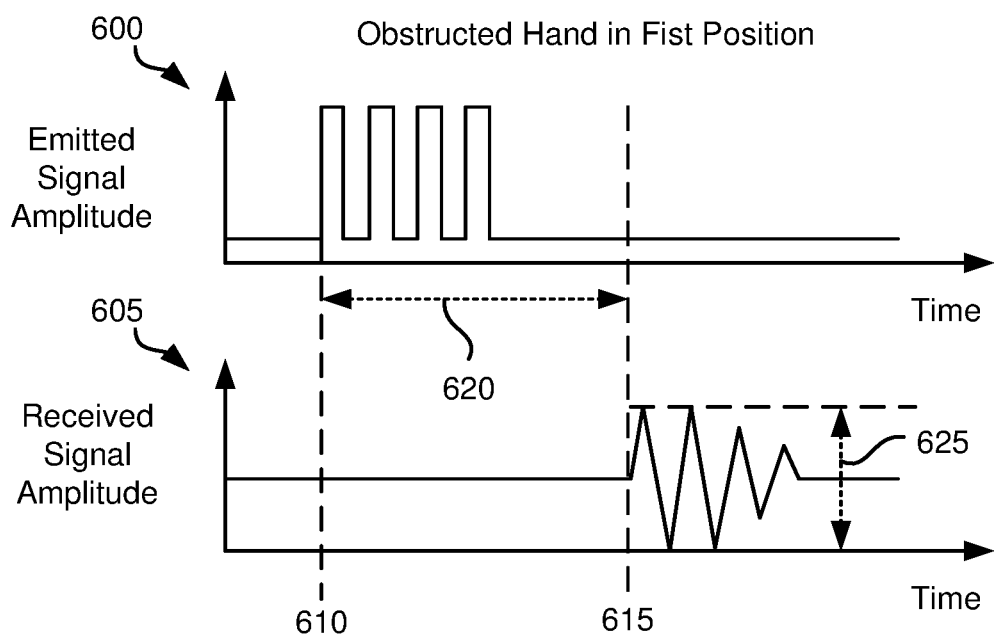
FIG. 6A is a diagram illustrating waveforms of an emitted and received ultrasound signal by the head-mounted display, according to one embodiment.

FIG. 6A is a diagram illustrating waveforms of an emitted and received ultrasound signal by the HMD 130, according to one embodiment. The graph 600 shows that an ultrasound signal is emitted by the ultrasound sensor 170 of the HMD 130 at a time indicated by timestamp 610. In FIG. 6A, the emitted ultrasound signal is represented as a rectangle function including four pulses, though it should be noted that, in other embodiments, the ultrasound signal may be represented by other types of functions and include any number of pulses. The ultrasound interface 235 can adjust the number of pulses, as well as the frequency of the pulses and the amplitude of the pulses. The amplitude and frequency of the pulses may vary over time.

The graph 605 (on the same time axis as graph 600) shows that an ultrasound signal is received by the ultrasound sensor 170 at a time indicated by timestamp 615. The received ultrasound signal is the emitted ultrasound signal that has reflected off of an obstructed hand of a user in a "fist" position. Thus, the peak-to-peak amplitude 625 of the received ultrasound signal may be less than that of the emitted ultrasound signal, e.g., due to signal attenuation through air. Further, the time of flight 620 represents the duration of time between when the ultrasound signal was emitted and received by the ultrasound sensor 170.

Figure 6B:
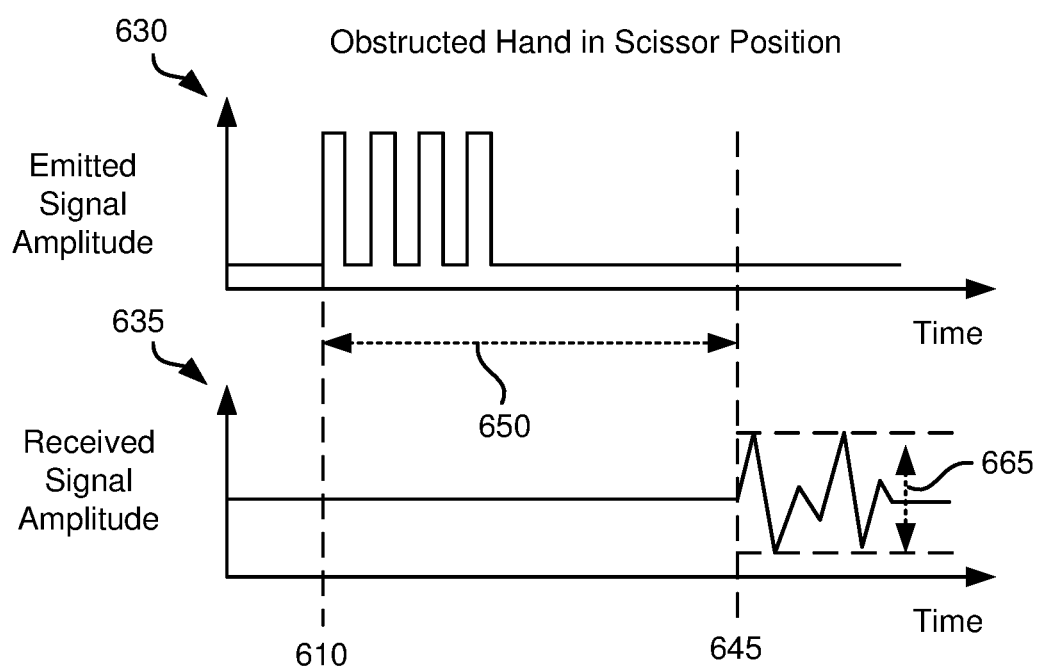
FIG. 6B is another diagram illustrating waveforms of an emitted and received ultrasound signal by the head-mounted display, according to one embodiment.

FIG. 6B is another diagram illustrating waveforms of an emitted and received ultrasound signal by the HMD 130, according to one embodiment. Graph 630 shows that an emitted ultrasound signal the same as illustrated in graph 600 of FIG. 6A is emitted at a time indicated by timestamp 610. The graph 635 (on the same time axis as graph 600 and 630) shows that an ultrasound signal is received by the ultrasound sensor 170 at a time indicated by timestamp 645. In contrast to FIG. 6A, the received ultrasound signal is the emitted ultrasound signal that has reflected off of an obstructed hand of a user in a "scissor" position instead of a "fist" position. Thus, the received ultrasound signal has different attributes than the received ultrasound signal in graph 605. In particular, the peak-to-peak amplitude 665 is less than the peak-to-peak amplitude 625 shown in graph 605, e.g., because ultrasound signals reflect differently off a user's hand depending on the position, orientation, and/or gesture of the hand. Furthermore, the received ultrasound signal in graph 635 undergoes a different signal transformation than the received ultrasound signal in graph 605. In particular, the received ultrasound signal in graph 605 has a "shape" with a gradually decreasing amplitude. In comparison, the received ultrasound signal in graph 635 has a different "shape" with two peaks in signal amplitude (e.g., the first and third pulses are greater in amplitude than the second and fourth pulses). The signal transformation or "shape" of the received ultrasound signal relative to the emitted ultrasound signal may vary based on the pose or gesture of the user's hands, for example, because parts of the hand (e.g., fingers or palm) reflect ultrasound signals differently. Thus, the received signal, which includes the summation of pulses that reflect off one or more hands and back to the ultrasound sensor 170, will vary. The time of flight 650 is also greater than the time of flight 620 shown in graph 605, e.g., because the hand in the "scissor" position is further away from the ultrasound sensor 170 than the hand in the "fist" position in FIG. 6A.

Figure 6C:
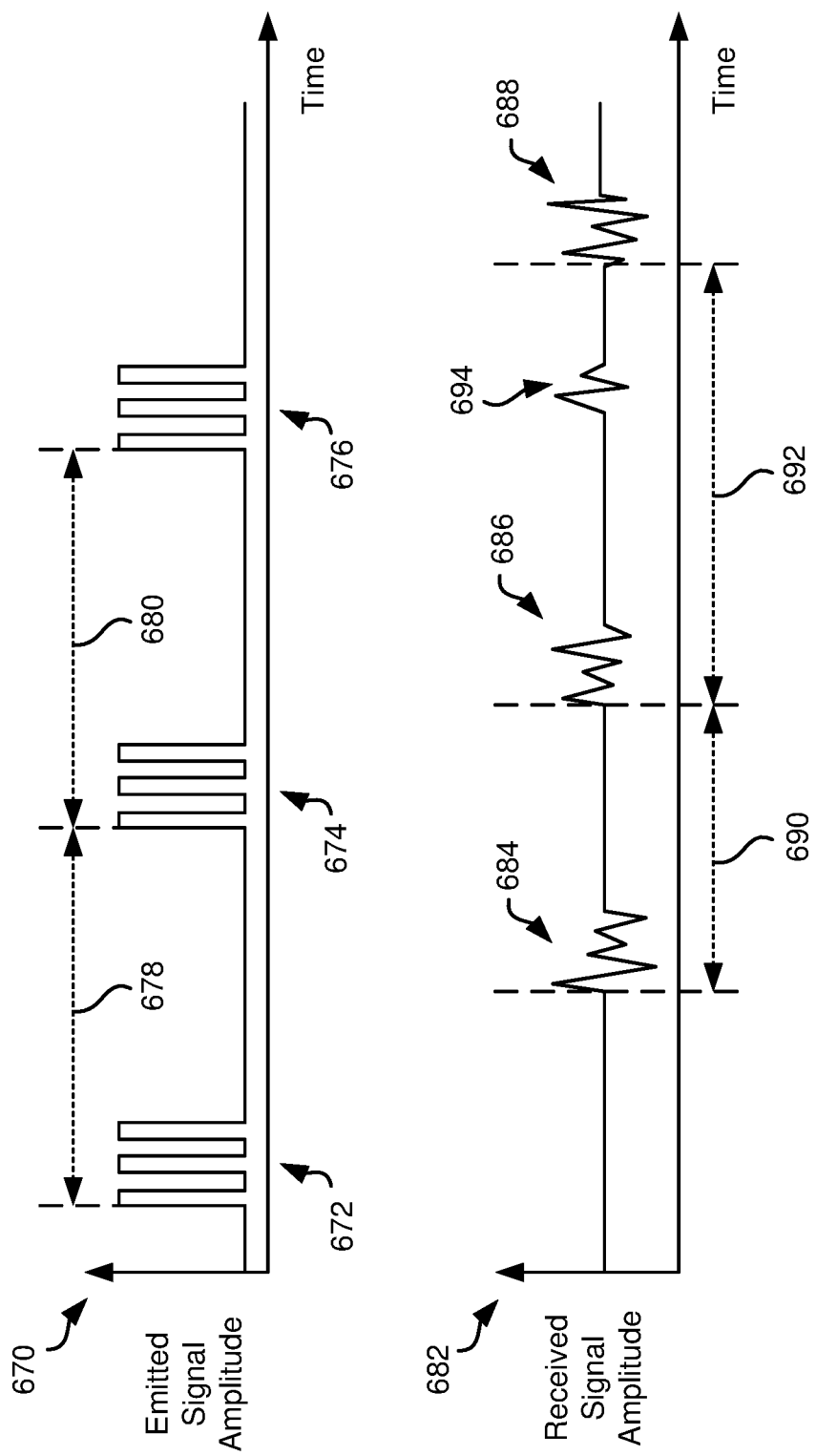
FIG. 6C is a diagram illustrating periods between emitted ultrasound signals and time delays between received ultrasound signals, according to one embodiment.

FIG. 6C is a diagram illustrating periods between emitted ultrasound signals and time delays between received ultrasound signals, according to one embodiment. The graph 670 shows three ultrasound signals 672, 674, and 676 emitted by the ultrasound sensor 170 of the HMD 130. The ultrasound sensor 170 emits the ultrasound signals at a constant period such that the period 678 between ultrasound signals 672 and 674 equals the period 680 between ultrasound signals 672 and 674. The ultrasound interface 235 can adjust the constant period.

The graph 682 (on the same time scale as graph 670) shows three ultrasound signals 684, 686, and 688 received by the ultrasound sensor 170. The ultrasound signals 684, 686, and 688 correspond to the emitted ultrasound signals 672, 674, and 676, respectively, which reflected off of a surface or object, for instance, a hand of a user. Unlike the constant periods between each of the emitted ultrasound signals, the time delay between consecutive received ultrasound signals may vary. In particular, the time delay 690 between received ultrasound signals 684 and 686 is less than the time delay 692 between received ultrasound signals 686 and 688. The difference in the time delays may be due to the user performing a hand gesture. If the user's hand is held in the same position, then the time delays may remain approximately the same because the time of flight for each reflected ultrasound signal is approximately constant (assuming a constant period of the emitted ultrasound signals). However, if the user's hand is moving during the hand gesture, then the time of flight varies between different reflected ultrasound signals.

In some embodiments, the ultrasound interface 225 can identify artifacts in the ultrasound data. For example, in the received ultrasound data shown in graph 682, there is an artifact 694 that is a received signal that does not correspond to ultrasound signal emitted by the ultrasound sensor 170. Artifacts may be due to background noise received by the ultrasound sensor 170, defects in the components of the ultrasound sensor 170, or other factors. The ultrasound interface 225 can identify an artifact based on a timestamp of the artifact. For instance, the artifact 694 is received while the ultrasound sensor 170 is emitting the ultrasound signal 676. The ultrasound interface 225 determines that the artifact 694 does not correspond to the emitted ultrasound signal 676 (or any previously emitted ultrasound signal) because not enough time has elapsed for the emitted ultrasound signal 676 to reflect off of a hand of a user.

Example Method of Hand Tracking

FIG. 7 is a flowchart illustrating a process 700 of performing hand tracking using the HMD 130, according to one embodiment. In some embodiments, one or more of the steps of the process 700 are performed by the processor 190—e.g., components of the process 190 described with reference to FIG. 2—within the system shown in FIG. 1. The process 700 may include different or additional steps than those described in conjunction with FIG. 7 in some embodiments or perform steps in different orders than the order described in conjunction with FIG. 7.

In one embodiment, the camera 145 (via the camera interface 220) captures 710 images in a region in front of a HMD 130 worn by a user to generate image data. The ultrasound sensor 170 emits 720 an ultrasound signal towards the region in front of the HMD 130. The ultrasound sensor 170 includes at least an ultrasound transmitter and an ultrasound receiver. In response to emitting the ultrasound signal, the ultrasound sensor 170 detects 730 a reflected version of the emitted ultrasound signal at an ultrasound receiver of the ultrasound sensor 170 (coupled to the HMD 130). The ultrasound interface 225 generates 740 ultrasound data by digitally processing the detected ultrasound signal. The tracking engine 235 processes 750 the image data and the ultrasound data to determine a pose or a gesture of the user's hands.

In some embodiments, the tracking engine 235 uses a machine learning model trained using feature vectors, where the machine learning model determines hand poses and gestures of one or more body parts of the user (e.g., the user's hands). The feature vectors may be based on previously generated ultrasound data. For example, a feature vector includes information describing the time delay between consecutive received ultrasound signals in a set of received ultrasound signals. For instance, the time delays are 800 microseconds, 850 microseconds, 900 microseconds, 850 microseconds, and 800 microseconds. The feature vector may correlate this particular pattern of time delays to a particular position, orientation, and/or gesture of the user's hands. For example, the features vector correlates the above pattern of time delays with a waving hand gesture, e.g., because the time of flight of the received ultrasound signals varies as the user is waving the user's hand.

Feature vectors may also include information describing signal transformations of the received ultrasound signals relative to the emitted ultrasound signals. For example, the emitted ultrasound signal has a series of pulses with a constant amplitude, but the received ultrasound signal has pulses with varying amplitudes. The feature vector can correlate certain transformations of pulse amplitudes of the signal to hand poses or gestures.

In some embodiments, the machine learning engine 240 identifies the feature vectors also based on calibration data. Thus, a machine learning model trained using these feature vectors can learn to filter out received ultrasound signals or artifacts that do not correspond to hand poses and gestures of the user's hands. For instance, the machine learning model is trained to recognize hand poses and gestures within a threshold radius (e.g., one meter) of the HMD 130 because the user's hands are unlikely to extend beyond the threshold radius. Objects outside the threshold radius may include walls of a room where the user is located or a table in the room.

In some embodiments, the machine learning engine 240 trains multiple machine learning models and categorizes the machine learning models based on certain parameters. For example, the machine learning engine 240 categorizes the machine learning models based on demographic information of users of the HMD 130. For instance, a 25 year old male user has larger hands than an 8 year old female user. The machine learning engine 240 trains a first machine learning model using feature vectors based on previously generated ultrasound data in which the users of the HMD 130 were female users in the 5-10 year old age range. The machine learning engine 240 trains a second machine learning model using feature vectors based on previously generated ultrasound data in which the users of the HMD 130 were male users in the 20-30 year old age range.

The machine learning engine 240 can retrieve demographic information of a user wearing the HMD 130. For example, the user logs into an online system using the HMD 130. The online system includes a user profile of the user, and the user profile includes the user's demographic information. The network interface 210 receives the demographic information from the online system. Based on the demographic information, the machine learning engine 240 determines whether to use the first or second machine learning model. Thus, the determined hand poses and gestures may be more accurate because the selected machine learning model is customized to the particular type of user. In other embodiments, the machine learning engine 240 categorizes the machine learning models based on other types of parameters such as the geographical location of the user.

The machine learning engine 240 may periodically retrain machine learning models over time as the processor 190 receives new ultrasound data. In some embodiments, the machine learning engine 240 receives new ultrasound data from the console 110 or an online database of ultrasound data from HMDs used by a population of users of the system 100.

In some embodiments, the tracking engine 235 determines that a hand of the user is obstructed, e.g., based on the image data. The machine learning engine 240 provides the image data and the ultrasound data as input into the machine learning model. The tracking engine 235 determines hand poses and gestures of a hand of the user using the machine learning model.

While certain processes have been described as being performed offline, in other embodiments those processes may be performed in real time. While certain processed have been described as being performed in real time, in other embodiments those processes may be performed offline.

Whilst components of the embodiments described herein (for example, filters) have been implemented in software, it will be understood that any such components can be implemented in hardware, for example in the form of ASICs or FPGAs, or in a combination of hardware and software. Similarly, some or all of the hardware components of embodiments described herein may be implemented in software or in a suitable combination of software and hardware. It will be understood that the present invention has been described above purely by way of example, and modifications of detail can be made within the scope of the invention. Each feature disclosed in the description, and (where appropriate) the claims and drawings may be provided independently or in any appropriate combination.

Some portions of the above description describe the embodiments in terms of algorithmic processes or operations. These algorithmic descriptions and representations are commonly used by those skilled in the data processing arts to convey the substance of their work effectively to others skilled in the art. These operations, while described functionally, computationally, or logically, are understood to be implemented by computer programs comprising instructions for execution by a processor or equivalent electrical circuits, microcode, or the like. Furthermore, it has also proven convenient at times, to refer to these arrangements of functional operations as modules, without loss of generality. The described operations and their associated modules may be embodied in software, firmware, hardware, or any combinations thereof. In one embodiment, a software module is implemented with a computer program product comprising a non-transitory computer-readable medium containing computer program code, which can be executed by a computer processor for performing any or all of the steps, operations, or processes described.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the disclosure. This description should be read to include one or at least one and the singular also includes the plural unless it is obvious that it is meant otherwise.

What is claimed is:

1. A head-mounted display (HMD) comprising:
a body configured to secure to a user's face;
an ultrasound transmitter coupled to the body and facing away from the user's face, the ultrasound transmitter configured to emit an ultrasound signal towards a region in front of the HMD;
an ultrasound receiver coupled to the body and configured to generate ultrasound data corresponding to a reflected version of the emitted ultrasound signal received at the ultrasound receiver;
a camera coupled to the body and facing away from the user's face to capture images in the region in front of the HMD; and
a processor coupled to the ultrasound receiver and the camera, the processor configured to:
determine that a portion of a first hand of the user is obstructed by a second hand of the user in a field of view of the camera based on the captured images; and
responsive to determining that the portion of the first hand is obstructed by the second hand, determine a pose or a gesture of both of the user's hands including the obstructed portion of the first hand by using a machine learning model trained using feature vectors of previous ultrasound data and a corresponding hand pose or hand gesture.

2. The HMD of claim 1, wherein the ultrasound transmitter, the ultrasound receiver, and the camera each face the user's hands.

3. The HMD of claim 1, wherein at least one of the feature vectors includes a plurality of mappings of an attribute of the previous ultrasound data to at least one hand pose or hand gesture.

4. The HMD of claim 3, wherein the attribute indicates a time delay between a first reflected ultrasound signal received at the ultrasound receiver and a second reflected ultrasound signal received at the ultrasound receiver subsequent to the first reflected ultrasound signal.

5. The HMD of claim 1, wherein the processor is further configured to retrieve calibration data based on previous ultrasound data, wherein the pose or the gesture of the user's hands is generated by taking into account the calibration data.

6. The HMD of claim 5, wherein the calibration data indicates at least a mapping of an ultrasound signal time of flight value to an object in front of the user other than the first hand of the user.

7. The HMD of claim 1, wherein the pose or the gesture of the user's hands is indicated in at least two dimensions.

8. The HMD of claim 1, wherein the ultrasound transmitter generates the emitted ultrasound signal based on a windowed cardinal sine function, and wherein the processor is further configured to modify the ultrasound data using pulse compression to reduce a noise level of the ultrasound data for processing to determine the pose or the gesture of the user's hands.

9. A head-mounted display (HMD) comprising:
an ultrasound sensor; and
a processor comprising:
an ultrasound interface configured to receive ultrasound data from the ultrasound sensor;
a camera interface configured to receive image data from a camera;
a machine learning engine communicatively coupled to the ultrasound interface and the camera interface, the machine learning engine trained using feature vectors of previous ultrasound data and a corresponding hand pose or hand gesture and configured to:
determine that a portion of a first hand of a user is obstructed by a second hand of the user in a field of view of the camera based on the captured images; and
responsive to determining that the portion of the first hand is obstructed by the second hand, determine a pose or a gesture of both of the user's hands including the obstructed portion of the first hand.

10. The HMD of claim 9, wherein at least one of the feature vectors includes a plurality of mappings of an attribute of the previous ultrasound data to a hand pose or a hand gesture, at least one of the attributes indicating a time delay between a first reflected ultrasound signal received at the ultrasound sensor and a second reflected ultrasound signal received at the ultrasound sensor subsequent to the first reflected ultrasound signal.

11. A method comprising:
capturing images in a region in front of a head-mounted display (HMD) worn by a user to generate image data;
emitting an ultrasound signal towards the region in front of the HMD;
responsive to emitting the ultrasound signal, detecting a reflected version of the emitted ultrasound signal at an ultrasound sensor coupled to the HMD;
generating ultrasound data by digitally processing the detected ultrasound signal;
determining that a portion of a first hand of the user is obstructed by a second hand of the user in a field of view of the HMD based on the captured images; and
responsive to determining that the portion of the first hand is obstructed by the second hand, determining a pose or a gesture of both of the user's hands including the obstructed portion of the first hand by using a machine learning model trained using feature vectors of previous ultrasound data and a corresponding hand pose or hand gesture.

12. The method of claim 11, wherein the ultrasound sensor includes at least one ultrasound transmitter and at least one ultrasound receiver each facing the user's hands.

13. The method of claim 11, wherein at least one of the feature vectors includes a plurality of mappings of an attribute of the previous ultrasound data to at least one hand pose or hand gesture.

14. The method of claim 13, wherein the attribute indicates a time delay between a first reflected ultrasound signal received at the ultrasound sensor and a second reflected ultrasound signal received at the ultrasound sensor subsequent to the first reflected ultrasound signal.

15. The method of claim 11, further comprising retrieving calibration data based on previous ultrasound data, wherein the pose or the gesture of the user's hands is determined by taking into account the calibration data.

16. The method of claim 15, wherein the calibration data indicates at least a mapping of an ultrasound signal time of flight value to an object in front of the user other than the user's hands.

17. The method of claim 11, wherein the pose or the gesture of the user's hands is indicated in at least two dimensions.

18. The method of claim 11, wherein the emitted ultrasound signal is generated based on a windowed cardinal sine function, and wherein the method further comprises modifying the ultrasound data using pulse compression to reduce a noise level of the ultrasound data for determining the pose or the gesture of both of the user's hands.

* * * * *

UNITED STATES PATENT AND TRADEMARK OFFICE
CERTIFICATE OF CORRECTION

PATENT NO. : 10,572,024 B1
APPLICATION NO. : 15/668418
DATED : February 25, 2020
INVENTOR(S) : Elliot Saba et al.

Page 1 of 1

It is certified that error appears in the above-identified patent and that said Letters Patent is hereby corrected as shown below:

In the Claims

Column 14, Line 21, Claim 9, after "camera" insert -- and --.

Column 14, Lines 29-30, Claim 9, delete "captured images;" and insert -- image data; --.

Signed and Sealed this
Thirteenth Day of October, 2020

Andrei Iancu
*Director of the United States Patent and Trademark Office*